United States Patent
Rana et al.

(10) Patent No.: US 11,141,445 B2
(45) Date of Patent: Oct. 12, 2021

(54) BOTANICAL ANTIOXIDANTS

(71) Applicant: Innophos, Inc., Cranbury, NJ (US)

(72) Inventors: Jatinder Rana, Grand Rapids, MI (US); Kylie Mitchell, Pennington, NJ (US)

(73) Assignee: Innophos, LLC, Cranbury, NJ (US)

( * ) Notice: Subject to any disclaimer, the term of this patent is extended or adjusted under 35 U.S.C. 154(b) by 0 days.

(21) Appl. No.: 16/561,544

(22) Filed: Sep. 5, 2019

(65) Prior Publication Data

US 2020/0078430 A1 Mar. 12, 2020

Related U.S. Application Data

(60) Provisional application No. 62/728,113, filed on Sep. 7, 2018.

(51) Int. Cl.
*A61K 36/45* (2006.01)
*A61P 39/06* (2006.01)

(52) U.S. Cl.
CPC .............. *A61K 36/45* (2013.01); *A61P 39/06* (2018.01)

(58) Field of Classification Search
None
See application file for complete search history.

(56) References Cited

U.S. PATENT DOCUMENTS

| 6,440,471 | B2 | 8/2002 | Walker et al. |
| 9,371,313 | B2 * | 6/2016 | Woolford ............. C07D 407/14 |
| 2013/0115174 | A1 | 5/2013 | Lepelletier et al. |
| 2017/0028006 | A1 | 2/2017 | Ricard et al. |

FOREIGN PATENT DOCUMENTS

| WO | WO-9912541 A1 * | 3/1999 | ............... A61P 31/00 |
| WO | 2011088420 A1 | 7/2011 | |
| WO | WO-2011088420 A1 * | 7/2011 | ............... B65B 1/04 |

OTHER PUBLICATIONS

Mustarichie et al. (2014) World J. Pharmacy and Pharmaceutical Sciences, vol. 3, Issue 10, 194-210. (Year: 2014).*
Beecher (2009) Pharmaceutical Biology 42: Sup1: 2-20. (Year: 2009).*
Booth et al. (2012) Food and Chemical Toxicology, 50:3150-3165. (Year: 2012).*
Caljouw et al. (2014) J. Am. Geriatr. Soc. 62: 103-110. (Year: 2014).*
Elberry et al. (2010) Food and Chemical Toxicology 48: 1178-1184. (Year: 2010).*
Jurikova et al. (2019) Molecules 24: (21 pages) (Year: 2019).*
Mathison et al. (2014) Nutrition Research 34: 420-427 (Year: 2014).*
Oszmianski et al. (2016) J. Functional Foods 22: 232-242. (Year: 2016).*
Venskutonis et al. (2016) Acta Physiol. Plant 38:33 (13 pages). (Year: 2016).*
Yan et al. (2002) J. Agric. Food Chem. 50: 5844-5849. (Year: 2002).*
Yang et al. (2018) Biomed. Res. Intern. Article ID 8584136 (11 pages). (Year: 2018).*
PCT/US2019/049581 International Search Report, dated Dec. 20, 2019.
PCT/US2019/049581 Written Opinion of the International Searching Authority, dated Dec. 20, 2019.
Jayaprakasha, G. K., et al., Antibacterial and antioxidant activities of grape (*Vitis vinifera*) seed extracts, Food Res. Int., 2003, vol. 36, pp. 117-122.
Yao, L. H., et al., Flavonoids in Food and Their Health Benefits, Plant Foods Hum. Nutr., 2004, vol. 59, pp. 113-122.
Kuo, L. J. et al., [gamma]-H2AX—A Novel Biomarker for DNA Double-strand Breaks, in vivo, 2008, vol. 22, pp. 305-310.
Brown, P. N. et al., Determinatino of anthocyanis in cranberry fruit and cranberry fruit products by high-performance iquid chromatography with ultraviolet detection: single-laboratory validation, J AOAC Int., 2011, vol. 94(2), pp. 459-466.
Booth, N. L. et al., An innovative approach to the safety evaluation of natural products: Cranberry (*Vaccinium macrocarpon Aiton*) leaf aqueous extract as a case study, Food Chern. Toxicol., 2012, vol. 50, pp. 3150-3165.
Chen, A. Y. et al., A review of the dietary flavonoid, kaempferol on human health and cancer chemoprevention, Food Chem., 2013, vol. 138(4), pp. 2099-2107. doi:10.1016/j.foodchem.2012.11.139.
Lee, Lan-Sook et al., Quantitative analysis of major constituents in green tea with different plucking periods and their antioxidant activity, Molecules, 2014, vol. 19, pp. 9173-9186. doi:10.3390/molecules19079173.
Mathison, B. D. et al., Consumption of cranberry beverage improved endogenous antioxidant status and protected against bacteria adhesion in healthy humans: a randomized controlled study, Nutr. Res., 2014, vol. 34, pp. 420-427.
Teleszko, M. et al.. Comparison of phenolic compounds and antioxidant potential between selected edible fruits and their leaves, J. Funct. Foods, 2015, vol. 14, pp. 736-746.
Oszmianski, J. et al., Comparison of bioactive potential of cranberry fruit and fruit-based products versus leaves, J. Funct. Foods, 2016, vol. 22, pp. 232-242.
Ferlemi, Anastasia-Varvara et al.. Berry leaves: An alternative source of bioactive natural products of nutritional and medicinal value, Antioxidants, 2016, vol. 5, No. 17; doi:10.3390/antiox5020017.
Stebbins, N. B., Characterization and Mechanisms of Anthocyanin Degradation and Stabilization, Theses and dissertations, 2017, 2618. http://scholarworks.uark.edu/etd/2618.
Adinortey, M. B. et al., DNA Damage Protecting Activity and Antioxidant Potential of Launaea taraxacifolia Leaves Extract, J Nat. Sci. Biol. Med., 2018, vol. 9(1), pp. 6-13.
Neto, C., Cranberry and Its Phytochemicals: A Review of In Vitro Anticancer Studies, J. Nutr., 2007, vol. 137, p. 186S-193S.

(Continued)

*Primary Examiner* — Russell G Fiebig
(74) *Attorney, Agent, or Firm* — David LeCroy

(57) ABSTRACT

A botanical extract that exhibits antioxidant activity, wherein the botanical extract is at least an extract from the leaf of a plant from the genus *Vaccinium*.

5 Claims, 13 Drawing Sheets

(56) References Cited

OTHER PUBLICATIONS

Singh, A. P. et al., Isolation of Specific Cranberry Flavonoids for Biological Activity Assessment, Food Chem., 2009, vol. 116(4), pp. 963-968.

Biswas, N. et al., Identification of Phenolic Compounds in Processed Cranberries by HPLC Method, J. Nutr. Food Sci., 2013, vol. 3(1) doi:10.4172/2155-9600.1000181.

Weh, K.M. et al., Cranberries and Cancer: An Update of Preclinical Studies Evaluating the Cancer Inhibitory Potential of Cranberry and Cranberry Derived Constituents, Antioxidants, 2016, vol. 5(27); doi:10.3390/antiox5030027.

Caldas, A.P. et al., Cranberry antioxidant power on oxidative stress, inflammation and mitochondrial damage, Int. J. Food Prop., 2018, vol. 21(1), pp. 582-592.

\* cited by examiner

Procyanidin A1

Procyanidin A2

Procyanidin B1;EC (4β→8)-C
Procyanidin B2;EC (4β→8)-EC
Procyanidin B3;C-(4α→8)-C
Procyanidin B4;C-(4α→8)-EC Procyanidin B5;EC (4β→8)-EC
Procyanidin B6;C-(4α→8)-C
Procyanidin B7;BC (4β→8)-C
Procyanidin B8;C- (4α→8)-EC Quercetin Isoquercetin 6'-O-trans-Caffeoylarbutin Avircularin Procyanidin A1

Procyanidin A2

Procyanidin B1;EC (4β→8)-C
Procyanidin B2;EC (4β→8)-EC
Procyanidin B3;C (4α→8)-C
Procyanidin B4;C (4α→8)-EC Procyanidin B5;EC (4β→6)-EC
Procyanidin B6;C (4α→6)-C
Procyanidin B7;BC (4β→6)-C
Procyanidin B8;C (4α→6)-EC Monotropein, 6,7-Dihydro,
10-O-(4-hydroxy-e-cinnamayl)

Myricetin 3-arabinofuranoside

6'-O-trans-Caffeoylarbutin

Avircularin (PDA 280)

(PDA 350)

1. Cyanidin-3-galactoside (R=Gal)
2. Cyanidin-3-arabinoside (R=Ara)

3. Peonidin-3-galactoside (R=Gal)
4. Peonidin-3-arabinoside (R=Ara)

5. Malvidin-3-galactoside (R=Gal)

BOTANICAL ANTIOXIDANTS

CROSS REFERENCE TO RELATED APPLICATIONS

The present application claims the benefit of U.S. Patent Application No. 62/728,113, filed 7 Sep. 2018, the disclosure of which is incorporated herein in its entirety by reference.

BACKGROUND OF THE INVENTION

Field of the Invention

The present invention generally relates to inhibitors of oxidation-induced DNA damage, and more particularly to botanical inhibitors of oxidation-induced DNA damage, namely, cranberry (*Vaccinium macrocarpon*) leaves, and the use of such plant-based inhibitors as an antioxidant.

Oxygen is a highly reactive atom that is capable of becoming part of potentially damaging molecules called "free radicals". Free radicals, commonly known as reactive oxygen species ('ROS'), contain one or more unpaired electrons in their outermost orbital. Common examples of reactive oxygen species include peroxyl radical ($ROO^\bullet$), superoxide anion ($O_2^\bullet$), reactive hydroxyl ($OH^\bullet$), and hydrogen peroxide ($H_2O_2$) radicals. These free radicals are generated spontaneously in living organisms during metabolism. As free radicals are highly unstable, they react with other molecules in their vicinity (e.g., proteins, lipids, or DNA) to attain stability by taking electrons from those molecules, thereby causing damage to the cell and initiating a chain reaction of free-radical generation.

An imbalance between the generation of free radicals and cellular antioxidant can lead to oxidative stress. Oxidative stress occurs when an oxygen molecule splits into single atoms with unpaired electrons, which are called free radicals. Since electrons prefer to be in pairs, these free radicals scavenge the body to seek out other electrons in which to pair with, causing damage to cells, proteins, and DNA in doing so. The term oxidative stress is used to describe the condition of oxidative damage resulting when the critical balance between free radical generation and antioxidant defenses is unfavorable.

Oxidative stress, arising as a result of an imbalance between free radical production and antioxidant defenses, is associated with damage to a wide range of molecular species including lipids, proteins, and nucleic acids. An excess of oxidative stress can lead to the oxidation of lipids and proteins, which is associated with changes in their structure and functions. Short-term oxidative stress may occur in tissues injured by trauma, infection, heat injury, hypertoxia, toxins, and excessive exercise. These injured tissues produce increased radical generating enzymes (e.g., xanthine oxidase, lipogenase, cyclooxygenase) activation of phagocytes, release of free iron, copper ions, or a disruption of the electron transport chains of oxidative phosphorylation, producing excess ROS. Oxidative stress has been implicated in the etiology of several degenerative diseases, such as stroke, Parkinson's disease, Alzheimer's disease, rheumatoid arthritis, diabetes mellitus, peptic ulcer, gene mutations and cancer, heart and blood disorders, and inflammatory diseases. Oxidative stress is now thought to make a significant contribution to all inflammatory diseases (arthritis, vasculitis, glomerulonephritis, lupus erythematous, adult respiratory diseases syndrome), ischemic diseases (heart diseases, stroke, intestinal ischema), hemochromatosis, acquired immunodeficiency syndrome, emphysema, organ transplantation, gastric ulcers, hypertension and preeclampsia, neurological disorder (Alzheimer's disease, Parkinson's disease, muscular dystrophy), alcoholism, smoking-related diseases, and many others.

Antioxidants are capable of stabilizing, or deactivating, free radicals before they attack cells. Application of an external source of antioxidants can assist in coping with oxidative stress. These include synthetic antioxidants such as butylated hydroxytoluene and butylated hydroxyanisole; however, these synthetic antioxidants have recently been reported to be dangerous for human health. Thus, the search for effective, nontoxic, natural compounds with antioxidative activity has intensified in recent years.

Antioxidants are reducing agents, examples of which include nutrient-derived antioxidants such as ascorbic acid (Vitamin C), tocopherols and tocotrienols (Vitamin E), carotenoids, and polyphenols; antioxidant enzymes such as superoxide dismutase, glutathione peroxidase, and glutathione reductase; metal binding proteins such as ferritin, lactoferrin, albumin, and ceruloplasimin; and trace metals (e.g., zinc and molybdenum). These antioxidants can scavenge reactive oxygen species and inhibit the chain reaction by donating an electron to the free radical. The antioxidant defense system, supported by dietary antioxidants, protects the body from free radicals. However, during oxidative stress, antioxidants are insufficient to maintain homeostasis. In such instances, antioxidants can be given as supplements, the consumption of which can significantly reduce the risk for free radical-associated diseases.

Phytomedicine plays an important role in the management of most of these diseases, with plants being a potential source of natural antioxidants. Studies have shown that the consumption of polyphenolic compounds found in tea, fruits, and vegetables is associated with low risk of these diseases. Consequently, there is a growing research interest in plants that contain antioxidants and health-promoting phytoconstituents as potential therapeutic agents. Medicinal plants provide a safe, cost-effective, ecological alternative to chemical antioxidants, which can be toxic on prolonged exposure.

Superfoods, functional foods, food supplements, and nutraceuticals have been introduced to the food industry and have enriched the products thereof, contributing to its further growth. Berry fruits constitute a large group of functional foods or "superfoods", whose consumption delivers several health benefits beyond basic nutrition due to their high content of bioactive natural products.

Cranberry (*Vaccinium macrocarpon*) was introduced to European settlers by Native Americans, who used the berries for treating kidney stones and urinary tract health problems. Since then, cranberry has been used to treat a variety of ailments, including urinary tract infections, stomach ailments, scurvy, vomiting, and weight loss by a large portion of the North American population. There are a number of cranberry fruit extracts on the market, and cranberry fruit juice is a common and popular beverage alone or in combination with other juices. Further, there is excellent recognition by the public of the health benefits of cranberry fruit-based products.

A strong body of scientific research documents the contribution of the consumption of berries to the three targets of functional foods: (a) health maintenance; (b) reduced risk of obesity; and (c) reduced risk of chronic diet-related diseases (e.g., cardiovascular disease, type 2 diabetes, and metabolic syndrome). In addition to the fruits, the leaves of berry plants have been used in traditional remedies. Leaf extracts have often been used against several diseases, such as colds, urinary tract inflammation, diabetes, and ocular dysfunction by Native Americans and other populations.

Still, little is known about the composition of leaves of berry plants and their beneficial properties. It is known that the main bioactive compounds in berry leaves are similar to those found in their fruits (i.e., phenolic acids and esters, flavonols, anthocyanins, and procyanidins). It is also known that the concentrations of these compounds can vary from family to family within the genera *Vaccinium*.

As part of a healthy lifestyle and a well-balanced, wholesome diet, antioxidant supplementation is recognized as an important means of improving free radical protection. As noted above, there is a need for effective, nontoxic, natural compounds with antioxidant activity. The present invention provides one such solution.

BRIEF SUMMARY OF THE INVENTION

Disclosed herein is a composition comprising the botanical extract of the leaf of *Vaccinium macrocarpon*, wherein the botanical extract inhibits γ-H2AX activity. The botanical extract can be present in the composition in an amount of about 1.0 µg/mL or greater. Preferably, the botanical extract is present in an amount of about 1.0 µg/mL to about 1000.0 µg/mL.

Also disclosed herein is a dietary supplement having antioxidant properties. The supplement comprises a cranberry leaf extract in a therapeutically effective amount, wherein the cranberry leaf extract inhibits γ-H2AX activity. The cranberry leaf extract is present in the supplement in an amount of about 25.0 µg/mL to about 500.0 µg/mL.

The present invention further provides a method of inhibiting oxidation-induced DNA damage in a subject by administering a composition comprising the botanical extract of the leaf of *Vaccinium macrocarpon* at a concentration of about 1.0 µg/mL to about 1000.0 µg/mL. Preferably, the botanical leaf extract is present in the composition in an amount of about 25.0 g/mL to about 500.0 µg/mL.

DETAILED DESCRIPTION OF THE INVENTION

Figure 1:
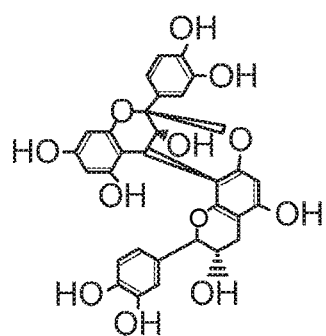
FIG. 1 provides the chemical structures of various procyanidin and flavonoid compounds identified in cranberry fruit extract (E1) (non-exhaustive).
Figure 1:
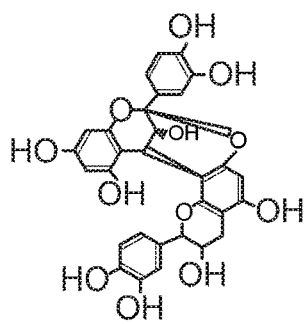
Figure 1:
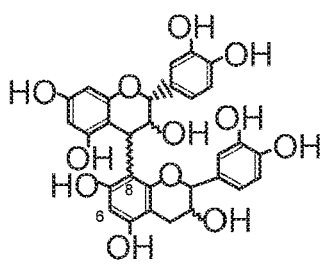
Figure 1:
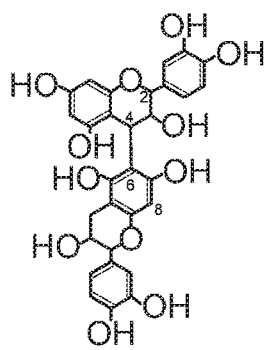
Figure 1:
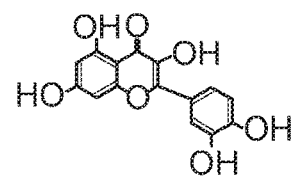
Figure 1:
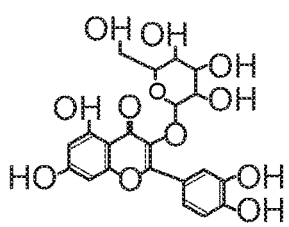
Figure 1:
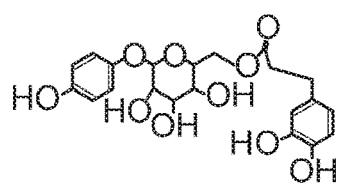
Figure 1:
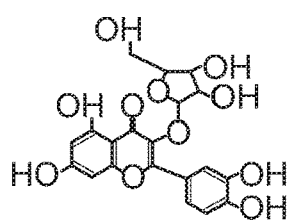
Figure 1:
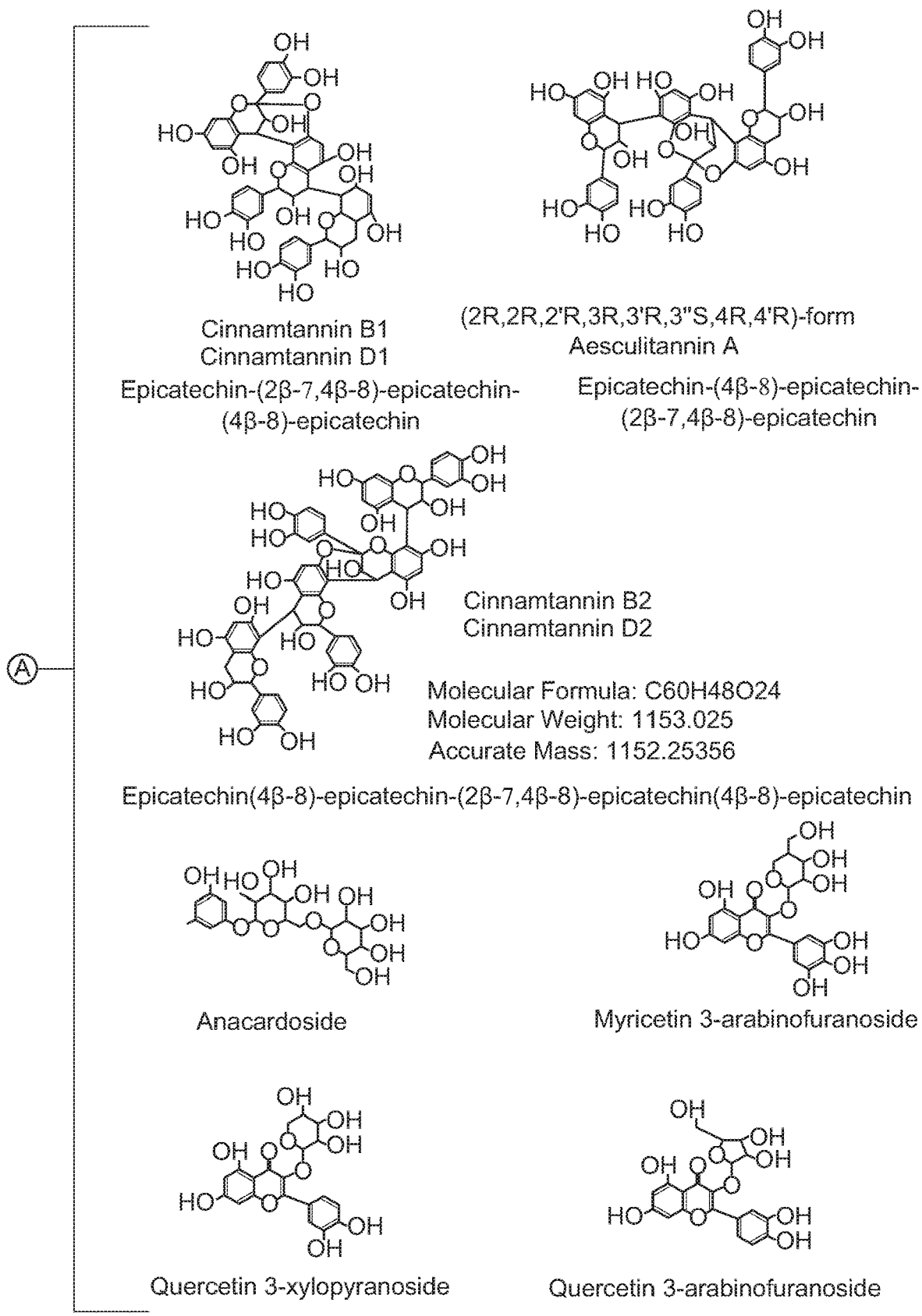

Disclosed herein is a botanical extract of the fruit and/or leaf of a plant comprising multiple procyanidins and bioflavonoids, wherein the fruit extract has been standardized to an anthocyanin content of about 1.90 mg/g, based on total weight of cyanidin-3-galactoside, cyaniding-3-arabinoside, peonidin-3-galactoside, peonidin-3-arabinoside, and malvidin-3-galactoside in the fruit extract, and wherein the botanical extract comprises at least an extract from the genus *Vaccinium*.

The present invention is further based on the surprising discovery that the leaf of the cranberry plant (*Vaccinium macrocarpon*) is substantially higher in certain flavonoids than the cranberry fruit. In particular, the extract from the leaves has a flavonoid content of at least 20 times greater than the flavonoid content of the fruit of the cranberry plant. In another embodiment, the extract from the leaves comprises a procyanidin trimers and procyanidin tetramers content of at least 23 times and 700 times greater than the procyanidin trimers and procyanidin tetramers content, respectively, of the fruit of the cranberry plant. Accordingly, in one embodiment, the botanical extract is from at least the leaves of *Vaccinium macrocarpon*. Further, the botanical extract is from at least the leaves of *Vaccinium macrocarpon* and exhibits antioxidant activity.

When the botanical extract is at least the leaf of the plant, the botanical extract can be present in the composition in an amount of about 1.0 µg/mL or greater. For example, the leaf extract can be present in the composition in an amount of about 1.0 µg/mL to about 1000.0 µg/mL.

For the present application, the term "composition" refers to a product that treats, improves, promotes, increases, manages, controls, maintains, optimizes, modifies, reduces, inhibits, or prevents a particular condition associated with a natural state, biological process or disease or disorder. For example, a composition improves the inhibition of oxidation and/or reduces inflammation, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment. Compositions can also include beverages, for example, beverages infused with an effective amount of an extract, or a tea satchel containing an effective amount of an extract. Non-limiting examples of food compositions containing an effective amount of an extract include baked goods, protein powders, meat products, dairy products, and confectionary.

As used herein, the term "extract" or "botanical extract" refers to a solid, viscid, or liquid substance or preparation that includes one or more active ingredients of a substance of at least the plant *Vaccinium* (e.g., *Vaccinium macrocarpon* and/or *Vaccinium oxycoccos*). Preferably, the active ingredient is derived from the extract of the leaf of the plant. The extract can be prepared using a solvent such as water, lower alcohols of 1 to 4 carbon atoms (e.g., methanol, ethanol, butanol, etc.), ethylene, acetone, hexane, ether, chloroform, ethylacetate, butylacetate, dichloromethane, N,N-dimethylformamide ('DMF'), dimethylsulfoxide ('DMSO'), 1,3-butylene glycol, propylene glycol, and combinations thereof, but also a fraction of the crude extract in such a solvent. So long as it assures the extraction and preservation of the active ingredient(s), any extraction method may be employed.

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving the inhibition of oxidation and/or reducing inflammation, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer," "administered," "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In preferred embodiments, oral routes of administering a composition are suitable.

As used herein, the term "subject" or "individual" includes mammals to which a composition may be administered. Non-limiting examples of mammals include humans, non-human primates, canines, felines, equines, bovines, rodents (including transgenic and non-transgenic mice) or the like. In some embodiments, the subject is a non-human mammal, and in some embodiments, the subject is human.

As used herein, the term "carrier" refers to a composition that aids in maintaining one or more plant extracts in a soluble and homogeneous state in a form suitable for administration, which is nontoxic and which does not interact with other components in a deleterious manner.

Unless indicated otherwise, all proportions and percentages recited throughout this disclosure are by weight.

The present invention provides plant-based inhibitor capable of inhibiting DNA damage due to oxidative stress. More particularly, the present invention is directed towards a botanical extract of the leaves of the cranberry plant from the genus *Vaccinium*. Such botanical extracts have been found to be capable of inhibiting oxidative stress-induced DNA damage by neutralizing free radicals, thereby terminating the chain reaction created by the free radicals. By terminating the chain reaction, damage due to the free radicals by their reaction with important macromolecules such as DNA, protein, lipids, or the cell membrane is prevented or inhibited.

Useful botanical extracts capable of inhibiting DNA damage due to oxidative stress according to the present invention include botanical extracts from the genus *Vaccinium*. More particularly, the botanical extract can be obtained from a plant chosen from *Vaccinium arctostaphylos, Vaccinium macrocarpon, Vaccinium oxycoccos, Vaccinium microcarpum, Vaccinium microcarpum, Vaccinium erythrocarpum, Vaccinium arboretum, Vaccinium crassifolium, Vaccinium angustifolium, Vaccinium boreale, Vaccinium caesariense, Vaccinium caespitosum, Vaccinium corymbosum, Vaccinium darrowii, Vaccinium deliciosum, Vaccinium elliotii, Vaccinium floribundum, Vaccinium hirsutum, Vaccinium membranaceum, Vaccinium myrsinites, Vaccinium myrtilloides, Vaccinium myvrtillus, Vaccinium ovalifolium, Vaccinium ovatum, Vaccinium padifolium, Vaccinium pallidum, Vaccinium parvifolium, Vaccinium praestans, Vaccinium reticulatum, Vaccinium scoparium, Vaccinium stamineum, Vaccinium tenellum, Vaccinium uliginosum. Vaccinium virgatum*, and/or *Vaccinium vitis-idaea*. Preferably, the botanical extract is at least from *Vaccinium macrocarpon. Vaccinium oxycoccos, Vacciniumn microcarpum*, and/or *Vaccinium microcarpum*. More preferably, the botanical extract is at least from *Vaccinium macrocarpon*; even more preferably a botanical extract from the leaf of *Vaccinium macrocarpon*.

Compositions capable of inhibiting DNA damage due to oxidative stress according to the present invention may include one or more compounds that may function as active ingredients and which are a component of the botanical extract. For example, the compound can be a phytochemical present in the plant from which the plant extract is obtained. The compound may be at least partially responsible for inhibiting DNA damage due to oxidative stress. The compound can be any compound capable of inhibiting DNA damage due to oxidative stress. In one embodiment, the compound is chosen from the phytochemicals isoquercetin, quercetin-3-glycoside, kaempferol glycoside, and/or procyanidins (e.g., A, B, trimer, tetramer).

Generally, one or more parts of a plant can be used to produce a botanical extract including, but not limited to, the root, the stem, the leaf, the flower, the fruit, the seed, and the testa of the seed. In the present invention, at least the leaf of the plant is used—alone or with other plant parts, particularly the fruit—to produce the plant extract. The fruit and leaf from the *Vaccinium* plant can be commercially obtained from various sources. The extract of the fruit and leaf can be obtained using any suitable extraction technique.

In this regard, one or more parts of the plant, particularly the leaf of the *Vaccinium* plant, can be collected and milled. Thereafter, the milled material can be extracted using a suitable solvent. The solvent can be removed in a concentration step. For example, the extracted material can be screened or filtered to create a supernatant and a cake. The cake can be pressed to remove a substantial portion of the liquid, which can be added to the supernatant. The cake can then be dehydrated and used as a fiber source. The supernatant can be distilled to remove the solvent or a portion thereof, to form a plant extract liquid concentrate. The removed solvent can be recycled. The concentrate can be dried (e.g., by spray drying) to provide a dried plant extract. This dried plant extract can be assayed and/or standardized as described herein. Preferably, the dried plant extract is derived from *Vaccinium macrocarpon*, particularly the leaf of the plant *Vaccinium macrocarpon*.

Suitable solvents for the extraction process include water, alcohol, or mixtures thereof. Exemplary alcoholic solvents include, but are not limited to, $C_1$-$C_7$ alcohols (e.g., methanol, ethanol, propanol, isopropanol, and butanol), hydroalcohols or mixtures of alcohol and water (e.g., hydroethanol), polyhydric alcohols (e.g., propylene glycol and butylene glycol), and fatty alcohols. Any of these alcoholic solvents can be used in the form of a mixture. In one embodiment, the plant extract is extracted using ethanol, water, or a combination thereof (e.g., a mixture of about 70% ethanol and about 30% water). In another embodiment, the plant extract is extracted using only water.

In one embodiment, the plant extract can be obtained using an organic solvent extraction technique. In another embodiment, solvent sequential fractionation can be used to obtain the plant extract. Total hydro-ethanolic extraction techniques can also be used to obtain the plant extract. Generally, this is referred to as a lump-sum extraction.

Total ethanol extraction can also be used. This technique uses ethanol as the solvent. This extraction technique can generate a plant extract having fat soluble and/or lipophilic compounds in addition to water soluble compounds.

Another example of an extraction technique that can be used to obtain the plant extract is supercritical fluid extraction ('SFE'). In this extraction procedure, the material to be extracted may not be exposed to any organic solvents. Rather, carbon dioxide can be used as the extraction solvent—with or without a modifier—in super-critical conditions (>31.3° C. and >73.8 bar). Those skilled in the art will appreciate that temperature and pressure conditions can be varied to obtain the best yield of extract. This technique can generate an extract of fat soluble and/or lipophilic compounds, similar to a total hexane and ethyl acetate extraction technique.

The botanical extract generated in the process can include a broad variety of phytochemicals present in the extracted material. The phytochemicals can be fat soluble or water soluble. Following collection of the extract solution, the solvent can be evaporated, resulting in the extract.

The botanical extract can be standardized to a specified amount of a particular compound. For example, the botanical extract can be standardized to a specified amount of an active ingredient or phytochemical present in the extract.

The amount of plant extract present in the oxidative stress-induced DNA damage inhibiting composition can depend upon several factors, including the desired level of oxidative stress-induced DNA damage inhibition, the oxidative stress-induced DNA damage inhibiting level of a particular plant extract or component thereof, and other factors. Preferably, the plant extract is present in an amount of from about 0.005 wt % or greater, for example, from about 0.005 wt % to about 99.00 wt %, based on total weight of the composition.

The oxidative stress-induced DNA damage inhibiting composition can include one or more acceptable carriers. The carrier can aid in enabling incorporation of the plant extract into an oxidative stress-induced DNA damage inhibiting composition having a suitable form for administration to a subject. A wide number of acceptable carriers are known in the art, and the carrier can be any suitable carrier. The carrier is preferable suitable for administration to animals, including humans, and can be able to act as a carrier without substantially affecting the desired activity of the plant extract and/or any active ingredient. The carrier can be chosen based upon the desired administration route and dosage form of the composition.

Suitable dosage forms include liquid and solid forms. In one embodiment, the composition is in the form of a gel, a syrup, a slurry, or a suspension. In another embodiment, the composition is in a liquid dosage form such as a drink shot or a liquid concentrate. In a further embodiment, the composition is present in a solid dosage form, such as a tablet, a pill, a capsule, a dragée, or a powder. When in liquid or solid dosage form, the composition can be in a food delivery form suitable for incorporation into food for delivery. Examples of suitable carriers for use in solid forms (particularly tablet and capsule forms) include, but are not limited to, organic and inorganic inert carrier materials such as gelatin, starch, magnesium stearate, talc, gums, silicon dioxide, stearic acid, cellulose, and the like. The carrier can be substantially inert.

As an example, silicified microcrystalline cellulose can be used as a carrier or binder. Silicified microcrystalline cellulose is a physical mixture of microcrystalline cellulose and colloidal silicon dioxide. One such suitable form of silicified microcrystalline cellulose is ProSolv SMCC® 90, available from Penwest Pharmaceutical Co., Patterson, N.J. Silicon dioxide, in addition to that provided by the silicified microcrystalline cellulose, may be added to the composition as a processing aid. For example, silicon dioxide can be included as a glidant to improve the flow of powder during compression in the manufacturing of solid dosage units, such as tablet.

In another embodiment, the carrier is at least a functional carrier such as buckwheat or spelt. By the addition of functional carriers into the composition, additional benefits may be provided such as lower glycemic index compared to standard carriers such as those mentioned above. Further, functional carriers can be allergan free (e.g., buckwheat), and by adding them into the production process, the botanical extracts of the invention may benefit from the flavonoids of these functional carriers, such as rutin and quercetin. Also, the high fiber content of these functional carriers may facilitate and regulate intestinal transit. Finally, the added mineral benefit of selenium found in spelt may aid in metabolism.

The oxidative stress-induced DNA damage inhibiting composition can include other inert ingredients, such as lubricants and/or glidants. Lubricants aid in the handling of tablets during manufacturing, such as during ejection from dies. Glidants improve powder flow during tablet compression. Stearic acid is an example of an acceptable lubricant/glidant.

The oxidative stress-induced DNA damage inhibiting composition can be made in solid dosage form, such as tablets and capsules. This form provides a product that can be easily transported by an individual to a place of eating, such as a restaurant, and taken prior to, during, or after consumption of a foodstuff. The composition can be formulated into dosage units containing suitable amounts of the plant extract and/or active ingredient that permit an individual to determine an appropriate number of units to take based upon appropriate parameters, such as body weight, foodstuff size, or carbohydrate (e.g., sugar) content.

In one embodiment, the botanical extract is present in the composition in a therapeutically effective amount, such as an amount of about 1.0 µg/mL or greater, preferably from about 1.0 µg/mL to about 1000.0 µg/mL, more preferably from about 15.0 µg/mL to about 1000.0 µg/mL, even more preferably from about 25.0 µg/mL to about 500.0 µg/mL, and even more preferably from about 40.0 µg/mL to about 150.0 µg/mL. The composition can be administered as a single dose, or in multiple doses. In one example, the compound is administered in up to three doses per day. For example, the compound may be administered prior to a meal, during a meal, or after a meal. In one embodiment, the composition is a dietary supplement having antioxidant properties containing cranberry leaf extract in a therapeutically effective amount.

The dosage can be chosen to provide a level of inhibitory effect in a single unit that may be effective for some individuals and/or some foodstuffs, while also allowing for relatively simple dosage increases to provide other levels of inhibitory effects that can be effective for other individuals and/or other foodstuffs.

The inhibiting composition can be in a form adapted for oral ingestion. This form can be configured as a single dosage form intended to provide a specified dose of the plant extract. For example, the single dosage form can be a powder, a pill, a tablet, a capsule, or a drink shot. The single dosage form can include, for example, from about 1.0 µg/mL to about 1000.0 µg/mL of the plant extract. Other forms include food or beverage compositions containing the plant extract.

EXAMPLES

Examples—Materials and Chemical Profiling

Example 1—Preparation of 70% Ethanol Extracts from Cranberry Fruit and Cranberry Leaf Dried Cranberry fruit powder (*Vaccinium macrocarpon*) (60 g) was loaded into three 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was automatically filtered and collected. The combined ethanol extract solution was evaporated with a rotary evaporator under vacuum to give a crude 70% ethanol fruit extract (E1).

Dried ground Cranberry leaf powder (*Vaccinium macrocarpon*) (140 g) was loaded into seven 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was automatically filtered and collected. The combined ethanol extract solution was evaporated with a rotary evaporator under vacuum to give a crude 70% ethanol leaf extract (E2).

The extraction results are provided in the following Table 1—

TABLE 1

Extraction of Cranberry fruit and Cranberry leaf

| Plant Part | Extract ID | Plant Powder (g) | Extract Weight (g) | Extraction Yield (wt %) |
|---|---|---|---|---|
| Fruit | E1 | 60 | 27.40 | 45.67% |
| Leaf | E2 | 140 | 23.75 | 16.96% |

Example 2—Chemistry Profiling of Cranberry Fruit and Cranberry Leaf Extracts

Flavonoid compounds present in the cranberry fruit extract E1 and cranberry leaf extract E2 were determined using ultra high pressure liquid chromatography ('HPLC') and mass spectrometry (ACQUITY® UPLC I-Class and XEVO® GS-XT-QT of system, both available from Water Corporation, Milford, Mass. USA). The column used was an ACQUITY® UPLC HSS T3 2.1×100 mm, 1.8 µm, with a column temperature of 40° C. and a sample temperature of 15° C. For the mobile phase, Solvent A was 10% acetonitrile ('ACN') in water (0.1% Formic Acid), and Solvent B was ACN. The acquisition range was 100-1500 Daltons ('Da'), and the acquisition mode was electrospray ionization ('ESI') (-). Table 2 below provides the HPLC conditions—

TABLE 2

HPLC condition for analyzing E1 and E2 extracts

| Extract | Run Time (min) | Injection Volume (µL) | Concentration |
|---|---|---|---|
| E1 | 20.00 | 1.00 | 5 mg/mL |
| E2 | 20.00 | 2.00 | 1 mg/mL |

Peak identification was based on accurate mass only. Multiple isomers may have been identified as the same compound due to the limitation of the database. For example, eight (8) procyanidin B1-B8 compounds having the same molecular weight of 578.528 were not differentiated in this analysis.

Procyanidins and flavonoid glycosides such as quercetin, isoquercetin, and myricetin 3-arabinofuranoside were detected and identified based on accurate mass in E1 at relatively low content. Chemical structures of compounds detected in E1 (non-exhaustive) are illustrated in FIG. 1. The following table lists compounds identified in E1 based on accurate mass—

TABLE 3

Compounds Identified in E1

| Compound Name | Neutral Mass (Da) | Observed Neutral Mass (Da) | Observed m/z | Mass error (ppm) | Observed RT (min) | Detector counts |
|---|---|---|---|---|---|---|
| Vaccihein A | 378.09508 | 378.0935 | 377.0862 | −4.3 | 0.65 | 22406 |
| Procyanidin B | 578.14243 | 578.1445 | 577.1373 | 3.6 | 0.66 | 13886 |
| 8-[5-(3,4-Dihydroxy-7-hydroxy-4-oxo-2H-1-benzopyran-2-yl]-2-hydroxyphenyl]-2,3-dihydro-7-hydroxy-2-(4-hydroxyphenyl)-4H-1-benzopyran-4-one | 510.13147 | 510.1291 | 509.1218 | −4.7 | 0.68 | 21507 |

TABLE 3-continued

Compounds Identified in E1

| Compound Name | Neutral Mass (Da) | Observed Neutral Mass (Da) | Observed m/z | Mass error (ppm) | Observed RT (min) | Detector counts |
|---|---|---|---|---|---|---|
| Procyanidin trimer | 864.19016 | 864.1939 | 863.1867 | 4.4 | 0.72 | 19512 |
| Monotropein | 390.11621 | 390.1165 | 389.1092 | 0.8 | 0.93 | 7503 |
| Orcinol gentiobioside, Anacardioside | 448.15808 | 448.1574 | 447.1501 | −1.6 | 3.20 | 22920 |
| 2-O-Benzoylglucose; D-form | 284.08960 | 284.0894 | 283.0822 | −0.6 | 3.54 | 18514 |
| Leptosin | 462.11621 | 462.1164 | 461.1091 | 0.4 | 3.59 | 51758 |
| Leptosin | 462.11621 | 462.1164 | 461.1091 | 0.4 | 3.63 | 38344 |
| 2-O-Benzoylglucose; D-form | 284.08960 | 284.0893 | 283.0820 | −1.0 | 3.71 | 6747 |
| Procyanidin trimer | 864.19016 | 864.1872 | 863.1800 | −3.4 | 3.79 | 5716 |
| Dunalianoside B | 450.11621 | 450.1150 | 449.1077 | −2.7 | 3.95 | 7628 |
| Dunalianoside B | 450.11621 | 450.1147 | 449.1074 | −3.5 | 4.12 | 7014 |
| Procyanidin trimer | 864.19016 | 864.1862 | 863.1789 | −4.6 | 4.15 | 45918 |
| 2-O-Benzoylglucose; D-form | 284.08960 | 284.0891 | 283.0819 | −1.6 | 4.17 | 6085 |
| Procyanidin tetramer | 1152.25355 | 1152.2530 | 1151.2457 | −0.5 | 4.37 | 5523 |
| Procyanidin trimer | 864.19016 | 864.1866 | 863.1793 | −4.1 | 4.98 | 5966 |
| Myricetin 3-arabinofuranoside | 450.07983 | 450.0793 | 449.0721 | −1.1 | 5.17 | 8296 |
| Myricetin 3-arabinofuranoside | 450.07983 | 450.0795 | 449.0723 | −0.6 | 5.51 | 16797 |
| Myricetin 3-arabiriofuranoside | 450.07983 | 450.0803 | 449.0730 | 1.0 | 5.64 | 46613 |
| Vaccinoside | 536.15299 | 536.1530 | 535.1457 | 0.0 | 5.78 | 28664 |
| Vaccinoside | 536.15299 | 536.1533 | 535.1460 | 0.6 | 5.97 | 72372 |
| Procyanidin A | 576.12678 | 576.1274 | 575.1201 | 1.1 | 6.13 | 119550 |
| Monotropein; 6,7-Dihydro,10-O-(4-hydroxy-E-cinnamoyl) | 538.16864 | 538.1692 | 537.1620 | 1.1 | 6.16 | 57726 |
| Monotropein; 6,7-Dihydro,10-O-(4-hydroxy-E-cinnamoyl) | 538.16864 | 538.1699 | 537.1626 | 2.4 | 6.33 | 151522 |
| Vaccinoside | 536.15299 | 536.1536 | 535.1463 | 1.1 | 6.35 | 7992 |
| Avicularin | 434.08491 | 434.0858 | 433.0785 | 2.0 | 6.38 | 62923 |
| Vaccinoside | 536.15299 | 536.1534 | 535.1461 | 0.7 | 6.46 | 5222 |
| Avicularin | 434.08491 | 434.0860 | 433.0787 | 2.5 | 6.56 | 52683 |
| Avicularin | 434.08491 | 434.0859 | 433.0787 | 2.4 | 6.79 | 130113 |
| Myricetin 3'-methyl ether | 332.05322 | 332.0536 | 331.0463 | 1.1 | 9.83 | 10303 |
| 4-O-Acetyl-6-trans-caffeoylarbutin | 476.13186 | 476.1319 | 475.1247 | 0.1 | 12.14 | 12950 |

Figure 2:
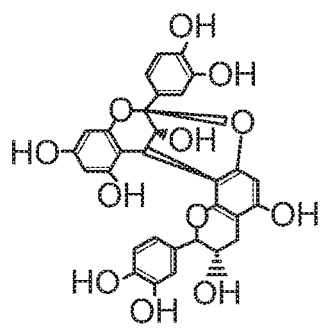
FIG. 2 provides the chemical structures of various procyanidin and flavonoid compounds identified in cranberry leaf extract (E2) (non-exhaustive).
Figure 2:
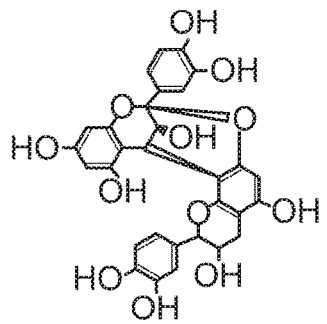
Figure 2:
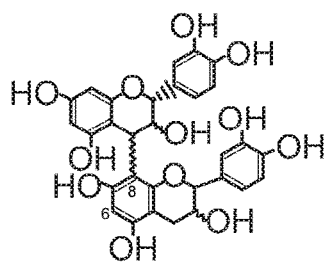
Figure 2:
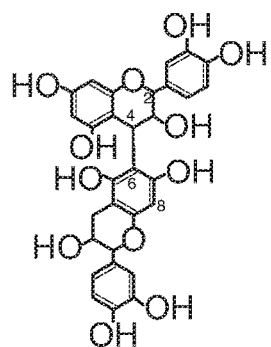
Figure 2:
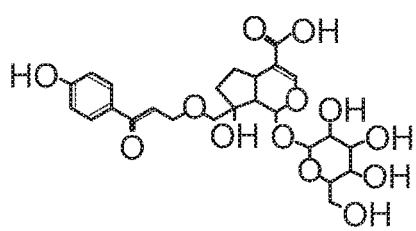
Figure 2:
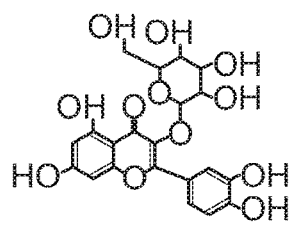
Figure 2:
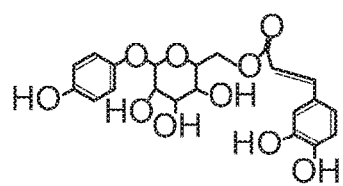
Figure 2:
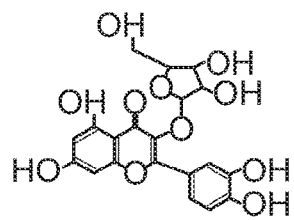
Figure 2:
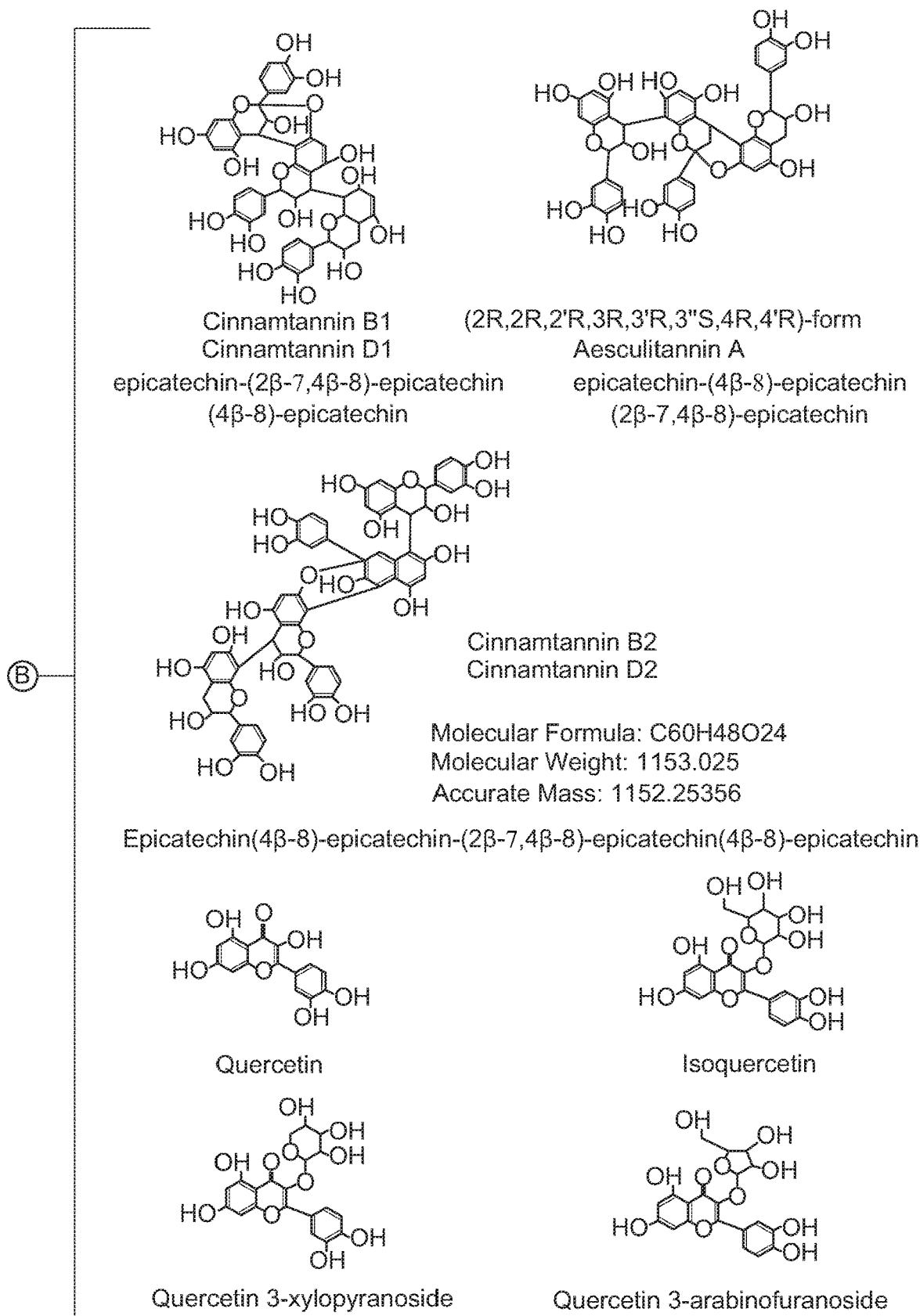

Abundant bioflavonoids were identified in E2, including avicularin, isoquercetin, kaempferol, glycosides, and others. Chemical structures of compounds detected in E2 (non-exhaustive) are illustrated in FIG. 2. The following table lists compounds identified in E2 based on accurate mass—

TABLE 4

Compounds Identified in E2

| Compound Name | Neutral Mass (Da) | Observed Neutral Mass (Da) | Observed m/z | Mass error (ppm) | Observed RT (min) | Detector counts |
|---|---|---|---|---|---|---|
| Procyanidin B | 578.14243 | 578.1441 | 577.1368 | 2.8 | 0.67 | 13416 |
| Monotropein | 390.11621 | 390.1155 | 389.1082 | −1.8 | 0.72 | 31923 |
| Procyanidin trimer | 864.19016 | 864.1872 | 863.1799 | −3.4 | 0.75 | 9024 |
| Procyanidin tetramer | 1152.25355 | 1152.2512 | 1151.2439 | −2.0 | 0.75 | 33165 |
| Myricetin 3-arabinofuranoside | 450.07983 | 450.0792 | 449.0720 | −1.3 | 0.94 | 6589 |
| Monotropein | 390.11621 | 390.1166 | 389.1093 | 0.9 | 0.94 | 43918 |
| Procyanidin tetramer | 1152.25355 | 1152.2502 | 1151.2429 | −2.9 | 2.36 | 28086 |
| Procyanidin B | 578.14243 | 578.1411 | 577.1338 | −2.3 | 3.19 | 10152 |
| Orcinol gentiobioside, Anacardioside | 448.15808 | 448.1582 | 447.1510 | 0.3 | 3.19 | 480731 |
| Procyanidin trimer | 864.19016 | 864.1878 | 863.1806 | −2.7 | 3.25 | 104158 |
| Procyanidin tetramer | 1152.25355 | 1152.2502 | 1151.2429 | −2.9 | 3.28 | 34709 |
| Procyanidin A | 576.12678 | 576.1260 | 575.1188 | −1.3 | 3.29 | 6558 |
| Procyanidin B | 578.14243 | 578.1418 | 577.1345 | −1.2 | 3.35 | 31488 |
| Orcinol gentiobioside | 448.15808 | 448.1581 | 447.1508 | 0.1 | 3.41 | 55958 |
| Procyanidin tetramer | 1152.25355 | 1152.2493 | 1151.2420 | −3.7 | 3.60 | 22964 |
| Orcinol gentiobioside, Anacardioside | 448.15808 | 448.1574 | 447.1501 | −1.5 | 3.63 | 9322 |
| Procyanidin trimer | 864.19016 | 864.1872 | 863.1799 | −3.5 | 3.80 | 53828 |
| Dunalianoside B | 450.11621 | 450.1157 | 449.1084 | −1.2 | 3.94 | 20828 |
| Procyanidin trimer | 864.19016 | 864.1883 | 863.1811 | −2.1 | 4.16 | 262966 |
| Procyanidin tetramer | 1152.25355 | 1152.2507 | 1151.2434 | −2.5 | 4.38 | 89683 |
| Procyanidin A | 576.12678 | 576.1261 | 575.1188 | −1.2 | 4.38 | 13405 |

TABLE 4-continued

Compounds Identified in E2

| Compound Name | Neutral Mass (Da) | Observed Neutral Mass (Da) | Observed m/z | Mass error (ppm) | Observed RT (min) | Detector counts |
|---|---|---|---|---|---|---|
| Procyanidin trimer | 864.19016 | 864.1870 | 863.1797 | −3.6 | 4.54 | 9939 |
| Procyanidin trimer | 864.19016 | 864.1885 | 863.1812 | −2.0 | 4.98 | 98041 |
| Procyanidin A | 576.12678 | 576.1262 | 575.1190 | −0.9 | 4.99 | 9959 |
| Procyanidin A | 576.12678 | 576.1257 | 575.1185 | −1.8 | 5.10 | 22194 |
| Procyanidin tetramer | 1152.25355 | 1152.2495 | 1151.2423 | −3.5 | 5.14 | 21067 |
| Procyanidin tetramer | 1152.25355 | 1152.2490 | 1151.2417 | −4.0 | 5.26 | 14044 |
| Procyanidin A | 576.12678 | 576.1264 | 575.1191 | −0.7 | 5.26 | 7671 |
| Procyanidin trimer | 864.19016 | 864.1871 | 863.1798 | −3.6 | 5.34 | 9598 |
| Procyanidin A | 576.12678 | 576.1246 | 575.1173 | −3.8 | 5.47 | 6853 |
| Procyanidin tetramer | 1152.25355 | 1152.2491 | 1151.2419 | −3.8 | 5.47 | 17471 |
| Procyanidin trimer | 864.19016 | 864.1873 | 863.1800 | −3.3 | 5.53 | 11401 |
| Myricetin 3-arabinofuranoside | 450.07983 | 450.0804 | 449.0732 | 1.4 | 5.63 | 22203 |
| Vaccinoside | 536.15299 | 536.1531 | 535.1458 | 0.1 | 5.78 | 98913 |
| Dunalianoside B | 450.11621 | 450.1164 | 449.1091 | 0.4 | 5.83 | 5653 |
| Vaccinoside | 536.15299 | 536.1531 | 535.1459 | 0.3 | 5.97 | 153237 |
| Procyanidin A | 576.12678 | 576.1275 | 575.1202 | 1.3 | 6.12 | 398543 |
| Procyanidin tetramer | 1152.25355 | 1152.2502 | 1151.2429 | −2.9 | 6.12 | 35819 |
| Jeediflavanone | 558.11621 | 558.1170 | 557.1097 | 1.4 | 6.12 | 5855 |
| Monotropein; 6,7-Dihydro,10-O-(4-hydroxy-E-cinnamoyl) | 538.16864 | 538.1696 | 537.1623 | 1.7 | 6.15 | 208791 |
| Procyanidin trimer | 864.19016 | 864.1890 | 863.1817 | −1.4 | 6.20 | 65398 |
| Monotropein; 6,7-Dihydro,10-O-(4-hydroxy-E-cinnamoyl) | 538.16864 | 538.1693 | 537.1620 | 1.2 | 6.33 | 353675 |
| Vaccinoside | 536.15299 | 536.1530 | 535.1457 | 0.0 | 6.35 | 6705 |
| Avicularin | 434.08491 | 434.0857 | 433.0785 | 1.9 | 6.38 | 512642 |
| Vaccinoside | 536.15299 | 536.1545 | 535.1472 | 2.8 | 6.47 | 9321 |
| Procyanidin A | 576.12678 | 576.1265 | 575.1192 | −0.5 | 6.47 | 11610 |
| Procyanidin tetramer | 1152.25355 | 1152.2511 | 1151.2438 | −2.1 | 6.47 | 33495 |
| Procyanidin trimer | 864.19016 | 864.1892 | 863.1819 | −1.1 | 6.48 | 113767 |
| Avicularin | 434.08491 | 434.0859 | 433.0787 | 2.4 | 6.56 | 916754 |
| 4-Hydroxyphenyl-gentioside | 434.14243 | 434.1441 | 433.1368 | 3.8 | 6.56 | 7559 |
| 3',4',4''',5',7,7'''-Hexahydroxy-8,3'''-biflavanone | 542.12130 | 542.1229 | 541.1156 | 3.0 | 6.59 | 7805 |
| 3,5-Bis(3,4-dihydroxycinnamoyl)quinic acide | 516.12678 | 516.1259 | 515.1186 | −1.7 | 6.61 | 6367 |
| Avicularin | 434.08491 | 434.0859 | 433.0786 | 2.2 | 6.78 | 1907961 |
| 2,4,6-Trihydroxyphenylacetic acid; 2-O-(3,4-Dihydroxybenzoyl) | 320.05322 | 320.0541 | 319.0468 | 2.6 | 7.08 | 8233 |
| Dunalianoside B | 450.11621 | 450.1165 | 449.1092 | 0.6 | 7.42 | 19468 |
| Procyanidin A | 576.12678 | 576.1246 | 575.1173 | 3.9 | 7.49 | 6252 |
| Lyonside | 552.22068 | 552.2212 | 551.2139 | 0.9 | 7.50 | 42922 |
| Quercetin 3-glycosides; Monosaccharides, 3-O-[3-Hydroxy-3-methylglutaroyl-(4)-Î ± L-rhamnopyranoside] | 592.14282 | 592.1432 | 591.1359 | 0.7 | 7.73 | 15267 |
| Leptosin | 462.11621 | 462.1171 | 461.1098 | 1.9 | 8.39 | 5097 |
| 8-[5-(3,4-Dihydroxy-7-hydroxy-4-oxo-2H-1-benzopyran-2-yl)-2-hydroxyphenyl]-2,3-dihydro-7-hydroxy-2-(4-hydroxyphenyl)-4H-1-benzopyran-4-one | 510.13147 | 510.1324 | 509.1251 | 1.8 | 8.63 | 8411 |
| Lyoniside | 552.22068 | 552.2210 | 551.2138 | 0.6 | 8.73 | 6492 |
| Procyanidin A | 576.12678 | 576.1270 | 575.1197 | 0.4 | 8.86 | 8440 |
| Procyanidin B | 578.14243 | 578.1420 | 577.1347 | −0.8 | 12.84 | 7997 |

Multiple procyanidins were found in E2 at substantially higher content compared to E1. Procyanidin dimers—including both A and B types—were found to be about fifty (50) times higher in E2 compared to E1 based on detector counts with mass-to-charge ratio ('m/z') at 575.11 and 577.13. Procyanidin trimers with observed m/z at 863.18 were present at about twenty-three (23) times higher in E2 compared to E1, whereas procyanidin tetramer with m/z at 1152.24 was over seven hundred (700) times higher in E2 compared to E1.

Similar bioflavonoids were also identified in E2 with much higher abundance, including isoquercetin, quercetin-3-arabinofuranoside, kaempferol glycoside, etc. based on LCMS analysis. Flavonoids with observed m/z at 463.093—identified with molecular formula $C_{21}H_{22}O_{10}$—are twenty (20) times higher for peak with retention time ('RT') at 6.38 min, and thirty-six (36) times higher for peak with RT at 6.78 min for E2 compared to corresponding peaks detected in E1. Overall detector counts of flavonoids in E2 are over twenty (20) times higher than flavonoids in E1 based on LCMS analysis.

Figure 3:
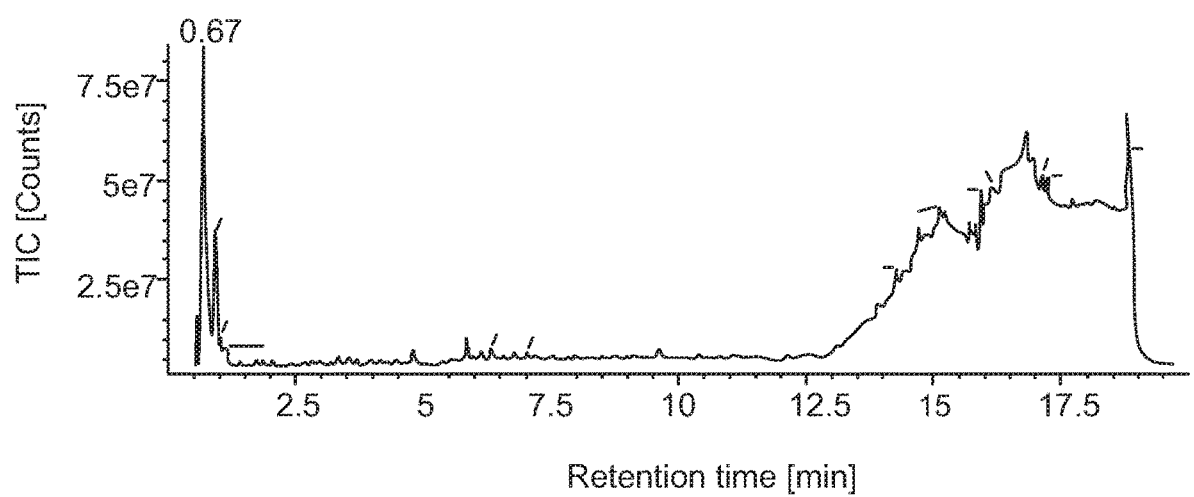
FIG. 3 is an LC/MS TIC chromatogram of cranberry fruit extract (E1).
Figure 4:
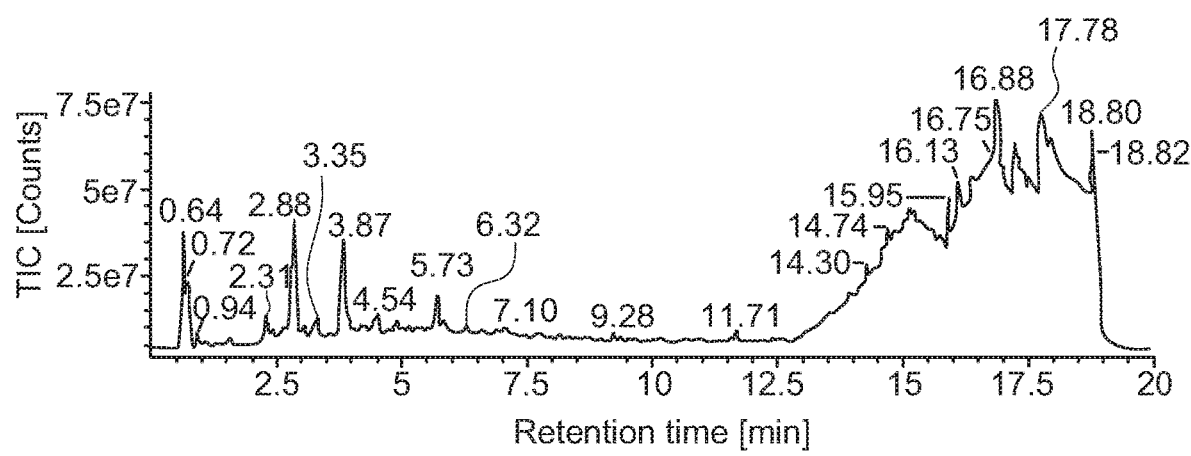
FIG. 4 is an LC/MS TIC chromatogram of cranberry leaf extract (E2).
Figure 5:
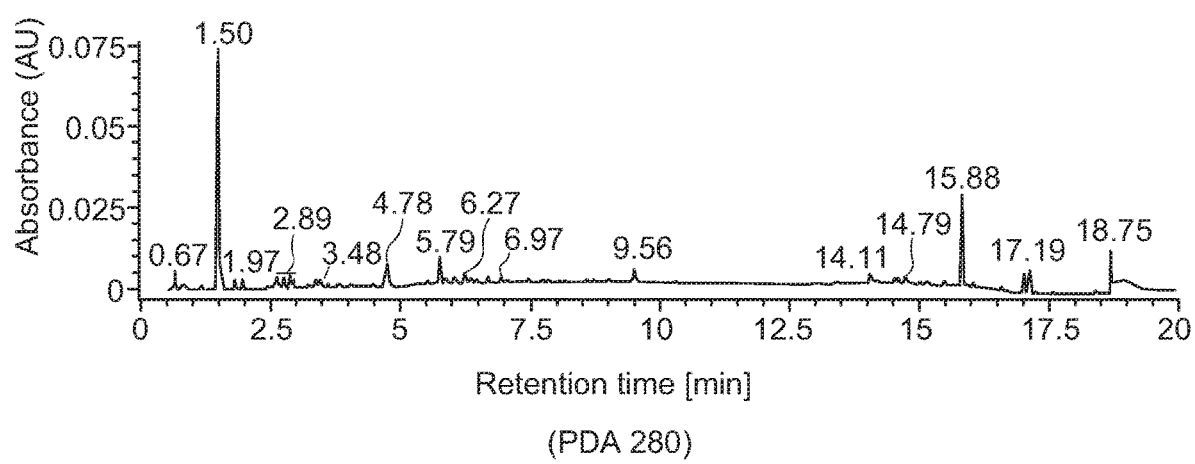
FIG. 5 is LC/PDA (wavelengths of 280 and 350 nm) chromatograms of cranberry fruit extract (E1).
Figure 5:
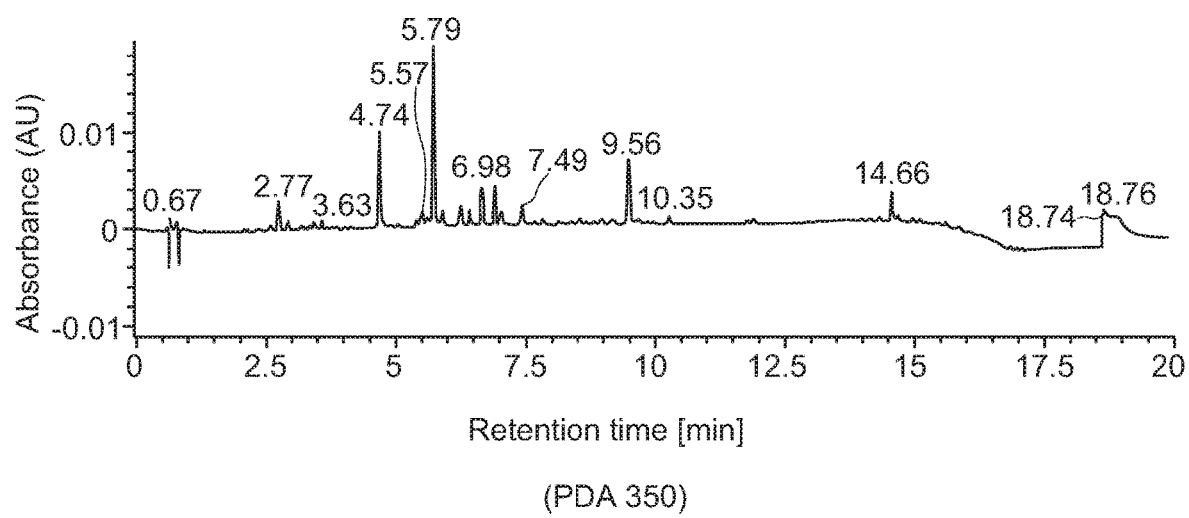

LCMS TIC, PDA 280 nm, and PDA 350 nm chromatograms are provided in FIG. 3 for E1 and FIG. 4 for E2. LCMS TIC chromatograms comparison between E2 and E1—illustrated in FIG. 5—clearly showed the higher contents for procyanidins and bioflavonoids in E2, while higher organic acid content was seen in E1 (FIG. 3).

Example 3—Anthocyanins Quantification

Anthocyanins quantification method was adapted from published HPLC analytical method (J. AGRIC. FOOD CHEM., "Separation, identification, quantification, and method validation of anthocyanins in botanical supplement raw materials by HPLC and HPLC-MS", Vol. 49(8), pp. 3515-3521 (2001)). HPLC system used was an Hitachi D7000 HPLC system, with a Phenomenex Luna 10 μm C18 column having a column size of 4.6×250 mm. Solvents used in the mobile phase were 0.5% phosphoric acid in $H_2O$ (Solvent A) and $H_2O$/ACN/Acetic Acid/$H_3PO_4$ (50%:48.5%: 1.0%:0.5%) (Solvent B). UV wavelength was 480 nm.

Reference standard cyanidin-3-glucoside was purchased from ChromaDex (Chicago, Ill. US). Cyanidin-3glucoside was prepared at 1 mg/mL concentration in 2% (v/v) HCl in methanol solution in 5 mL volumetric flask. The stock solution was further diluted by ⅕, ¹⁄₁₀, ¹⁄₂₀, and ¹⁄₁₀₀ times in 2% (v/v) HCl in methanol to give cyanidin-3-glucoside solutions at five concentrations of 1.00, 0.20, 0.10, 0.05 and 0.01 mg/mL, respectively. The five solutions were unitized to generate a calibration curve. Each sample was injected at 10 μL in three replicates. The calibration curve was determined based on the integrated peak areas. The correlation coefficient (R2) value of cyanidin-3-glucoside was determined at 0.9985.

Figure 7:
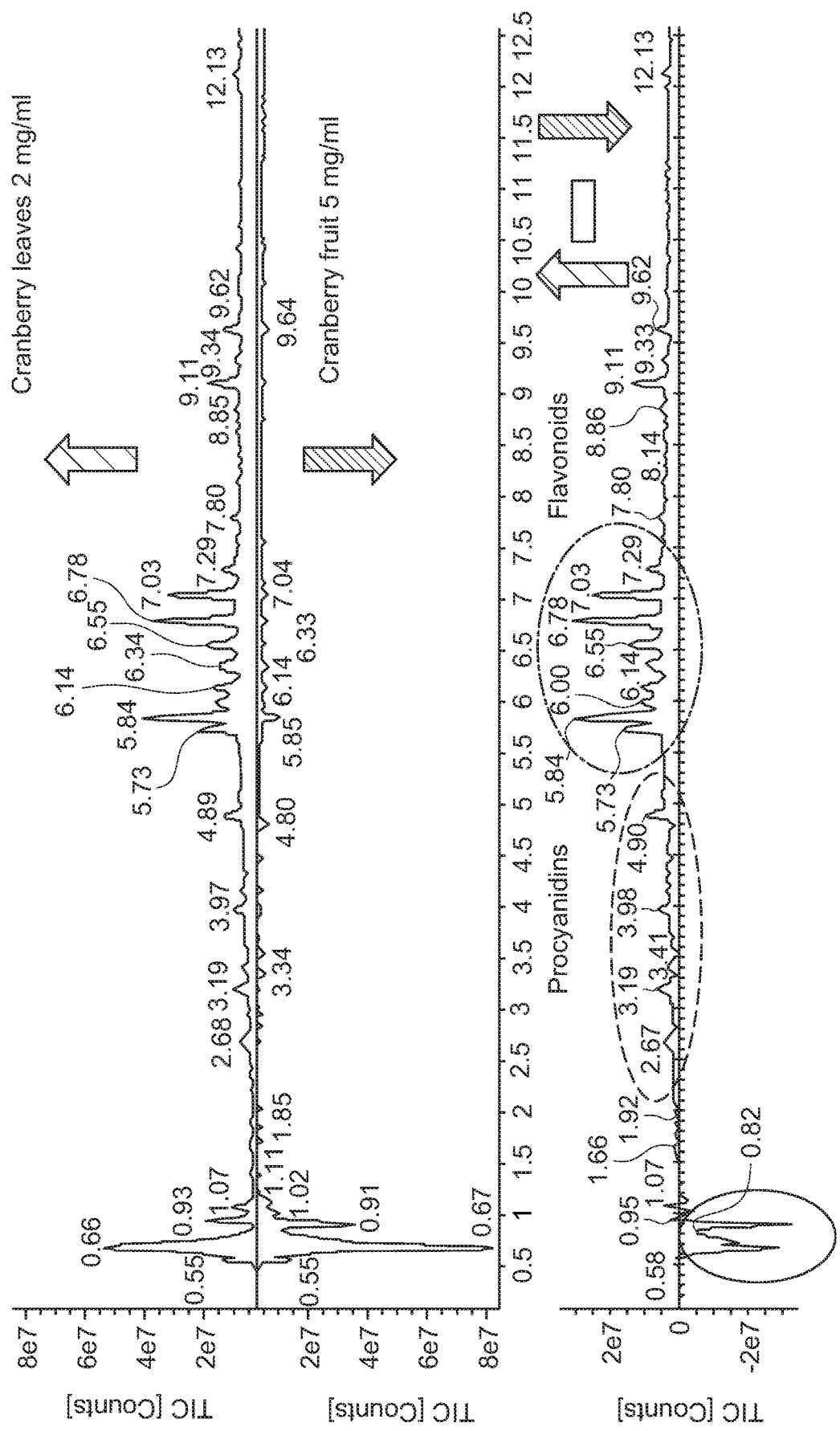
FIG. 7 is LC/MS TIC chromatograms comparison between cranberry fruit extract (E1) and cranberry leaf extract (E2).
Figure 8:
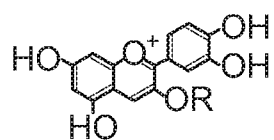
FIG. 8 provides the chemical structures of five anthocyanins identified in cranberry fruit extract (E1) present in the extract in an amount of 1.90 mg/g total anthocyanins.
Figure 8:
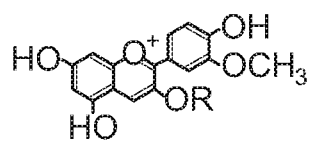
Figure 8:
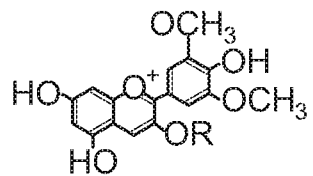
Figure 9:
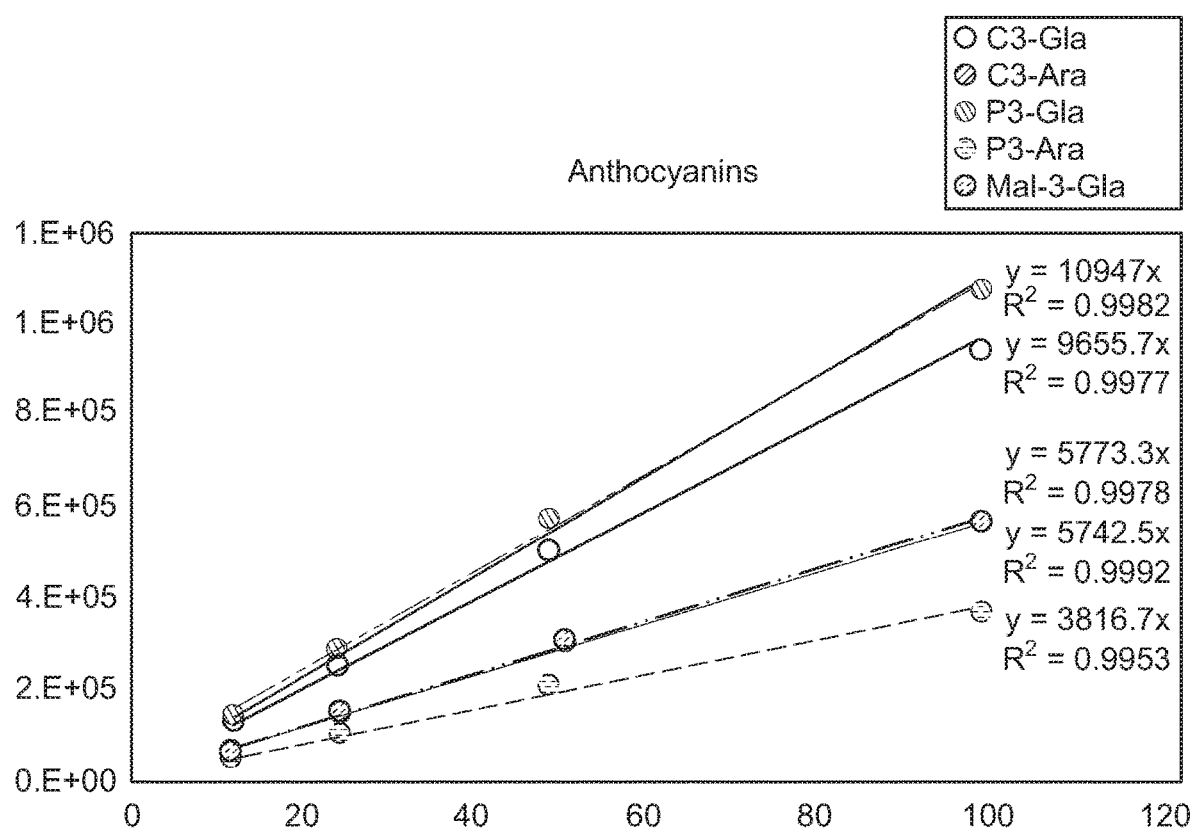
FIG. 9 is an illustration of the calibration curves of anthocyanins in cranberry fruit extract (E1).

Samples were prepared for analysis as follows, 12.5, 25.0, 50.0, and 100.0 mg of E1 were weighed. 1 mL of 2% (v/v) HCl in methanol was added to each sample, and then each sample was mixed by sonication for fifteen (15) minutes and vortexed at 10,000 rpm for five (5) minutes. 20 μL of supernatant of each solution was injected to HPLC in three replicates. Quantitative analysis of five (5) anthocyanin compounds at different concentrations demonstrated linearity with correlation coefficients $R^2$ from 0.9953 to 0.9982 (FIG. 7). The amount of each individual anthocyanin was calculated based on the integrated peak areas against cyaniding-3-glucoside at 0.05 mg/mL for the samples at a concentration of 25 mg/mL and 50 mg/mL, respectively.

Figure 6:
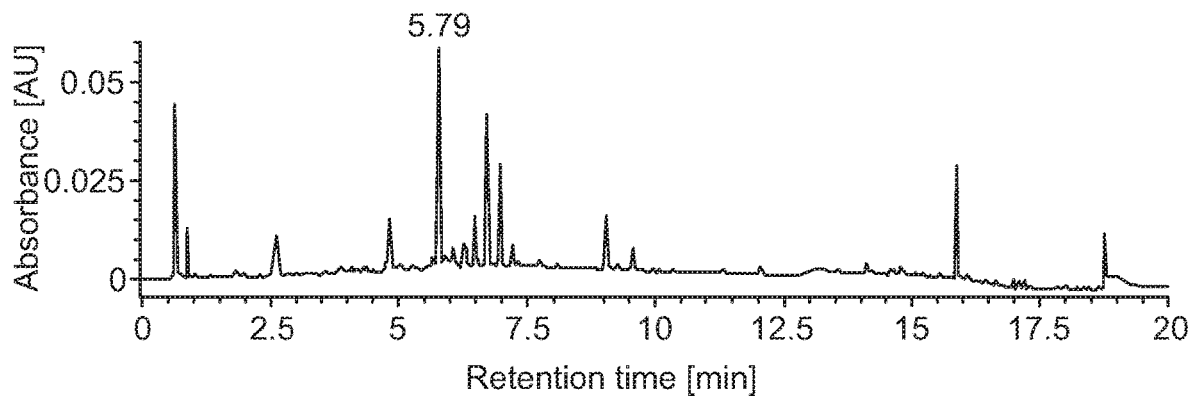
FIG. 6 is LC/PDA (wavelengths of 280 and 350 nm) chromatograms of cranberry leaf extract (E2).
Figure 6:
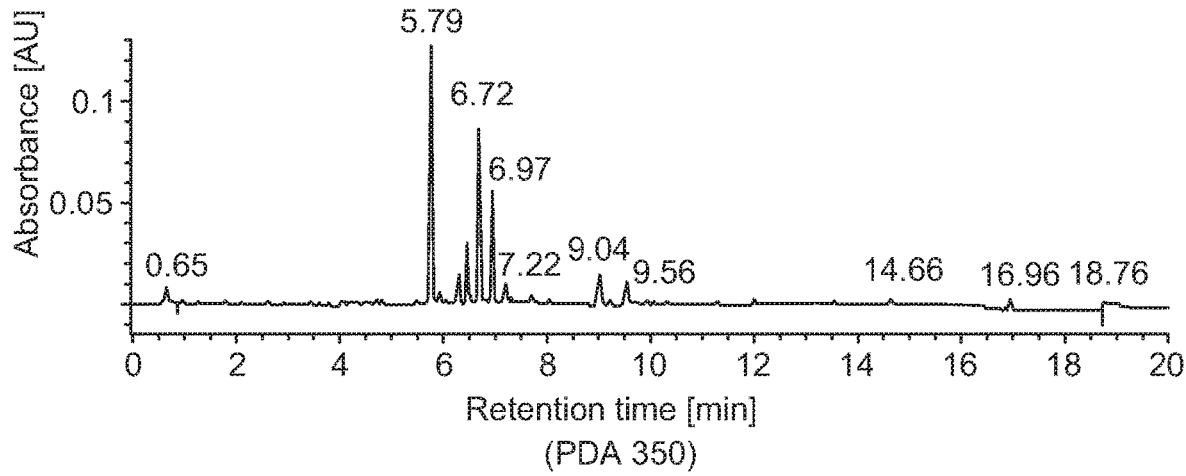

Five anthocyanins were quantified in E1 with a total content of 1.903 mg/g as of dry weight of E1. These anthocyanins included Cyanidin-3-galactoside ('C3Gla'), Cyanidin-3-arabinoside ('C3-Ara'), Peonidin-3-galactoside ('P3-Gla'), Peonidin-3-arabinoside ('P3-Ara'), and Malvidin-3-galactoside ('Mal3-Gla'), based on analysis and comparison with those disclosed in the analytical method article and the article J. AOAC INT., "Determination of anthocyanins in Cranberry fruit and Cranberry fruit products by High-Performance Liquid Chromatography with Ultraviolet Detection; Single-Laboratory Validation", Vol. 94(2); pp. 459-466 (2011). These compounds are illustrated in FIG. 6. No anthocyanins were detected in E2.

TABLE 3

Amount of five anthocyanins calculated in E1

| | mg/g R1 - 25 mg/mL | R1 - 50 mg/mL |
|---|---|---|
| C3-Gla | 0.506 | 0.503 |
| C3-Ara | 0.276 | 0.275 |
| P3-Gla | 0.591 | 0.587 |
| P3-Ara | 0.200 | 0.195 |
| Mal-3-Gla | 0.330 | 0.331 |

Examples—Bioassay

Extracts of Cranberry fruit and Cranberry leaf were prepared with food-grade ethanol, and then filtered and dried as described above. Research grade reagents were used for the rest of the assay preparations. Extracts were dissolved in dimethyl sulfoxide ('DMSO') to a final concentration of 50 mg/mL, and then diluted in appropriate buffer for each bioassay to working concentrations.

Example 4—DNA Damage Assay

When DNA damage—whether endogenous or exogenous—forms double stranded breaks ('DSBs'), it is always followed by phosphorylation of the histone H2AX. H2AX is a variant of the H2A protein family, which is a component of the histone octomer in nucleosomes. It is phosphorylated by kinases such as ataxia telangiectasia mutated ('ATM') and ATM-Rad3-related ('ATR') in the PI3K pathway. The protein γ-H2AX is the first step in recruiting and localizing DNA repair proteins. DSBs can be induced by mechanisms such as ionizing radiation or cytotoxic agents and subsequently, γ-H2AX foci quickly form. These foci represent the DSBs in a 1:1 manner and can be used as a biomarker for damage. An antibody can be raised against γ-H2AX, which can therefore be visualized by immunofluorescence through secondary antibodies The detection and visualization of γ-H2AX by flow cytometry allow the assessment of DNA damage, related DNA damage proteins, and DNA repair.

Human skin fibroblasts were seeded at a density of 8000 cells/well in 96-well tissue culture plates. After 24 hours, cells were treated with test compounds for 48 hours, after which the cells were treated with 1 mM hydrogen peroxide for 4 hours to induce DNA damage. Hydrogen peroxide induces DNA damage by creating breaks in the DNA. Cells were then fixed and stained with an antibody to the biomarker γ-H2AX, which is a phosphorylated histone variant that is found at double-strand breaks. At sites of double-strand breaks, the histones are phosphorylated, indicating that the DNA is damaged and requires repair. An antibody for γ-H2AX—the phosphorylated histone variant—is useful in identifying sites of DNA damage. Nuclei were stained with 4',6-diamidino-2-phenylindole ('DAPI'), which is a fluorescent stain that binds to DNA. Pictures were taken with Image Xpress and analyzed with Meta Xpress to measure fluorescence intensity in each condition divided by the total number of cells.

Figure 10:
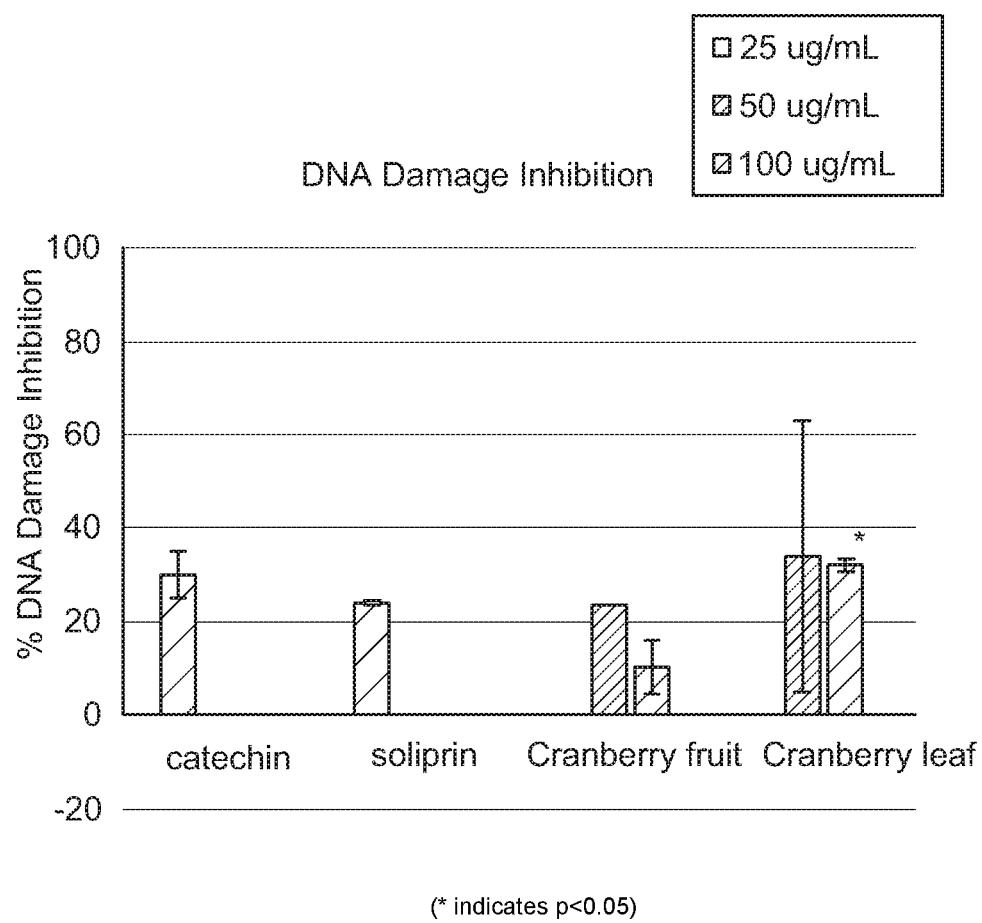
FIG. 10 is a graph illustrating the efficacy of cranberry fruit extract (E1) and cranberry leaf extract (E2) in inhibiting DNA damage compared to catechin and soliprin standards.

DNA damage in response to hydrogen peroxide treatment was measured by the amount of γ-H2AX present in cells. Cranberry fruit E1 and Cranberry leaf E2 extracts were tested for DNA damage inhibition at 50 and 100 μg/mL based on the amount of γ-H2AX detected after treatment with hydrogen peroxide to induce DNA damage. Catechin and soliprin at 25 μg/mL were used as positive controls. As shown in FIG. 10, cranberry leaf extract E2 at 100 μg/mL exhibited significant inhibition of DNA damage. Percent inhibition was calculated relative to wells that were not treated with extracts but were exposed to hydrogen peroxide. From this Example, it is seen that pre-treating fibroblasts with E2 at 100 μg/mL significantly reduced the amount of γ-H2AX detected, showing the ability of E2 to protect DNA from damage.

Figure 11:
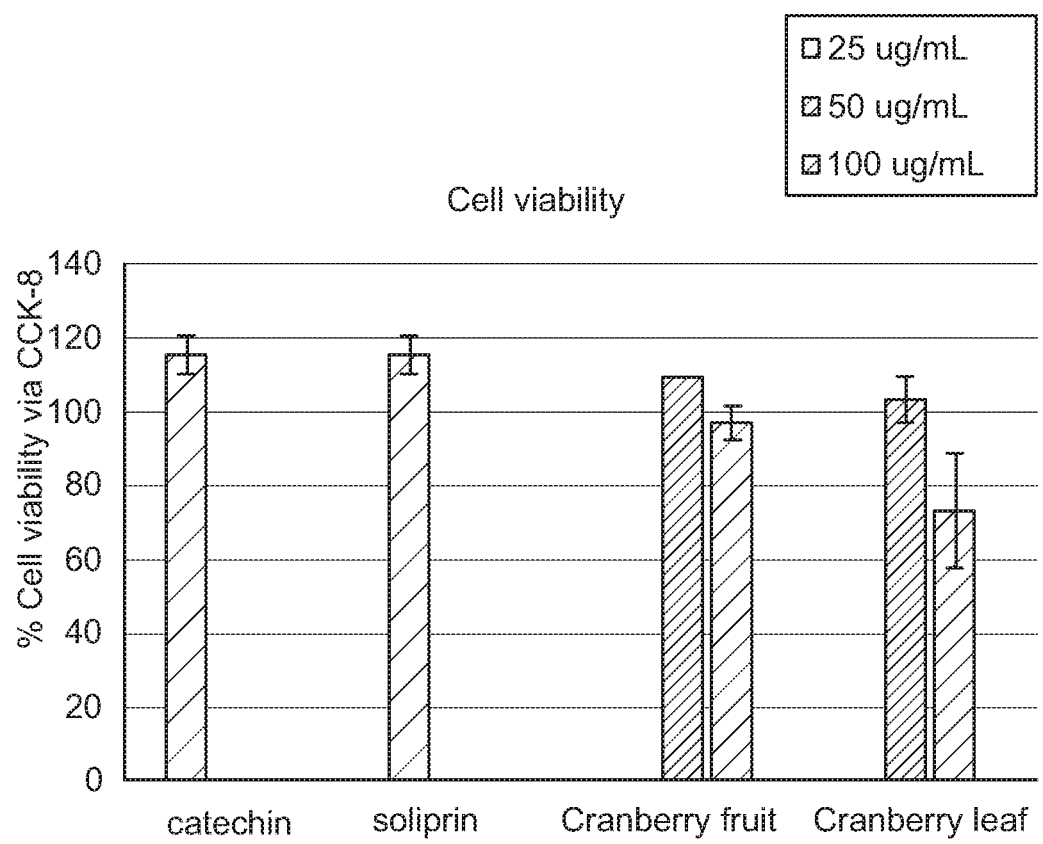
FIG. 11 is a graph illustrating cell viability of a cell culture when dosed with various doses of cranberry fruit extract (E1) and cranberry leaf extract (E2) versus catechin and soliprin standards.

Cell Counting Kit-8 ('CCK-8') was used to determine the percentage of viable cells in each treatment relative to an untreated control. CCK-8 reagent was added to the media (final concentration 10% total volume) and incubated for one (1) hour at 37° C. and 5% $CO_2$ before absorbance was read on a Multimode Reader at 460 nm to determine the number of viable cells relative to untreated control wells. None of the treatments was statistically significantly different from the untreated controls (FIG. 11).

The above data illustrates that the botanical extract of the leaf of *Vaccinium macrocarpon* has one or more compounds that exhibit anti-oxidant activity. More particularly, the cranberry leaf extract may have reasonable activities in ameliorating γ-H2AX activity.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Further, unless defined otherwise, all technical and scientific terms used herein have the same meaning as commonly understood to one of ordinary skill in the art to which this invention belongs. Consequently, it is not intended that this invention be limited to the specific embodiments disclosed herein, but that it cover all modifications and alternatives coming within the true scope and spirit of the invention as embodied in the attached claims.

We claim:

1. A method of inhibiting oxidation-induced DNA damage in a subject in need thereof comprising:
    administering an effective amount of a composition comprising a botanical extract of a leaf of *Vaccinium macrocarpon* to said subject,
    wherein the botanical extract is present in the composition in an amount of about 40.0 µg/mL to about 150.0 µg/mL,
    wherein the botanical extract is free of anthocyanins, and
    wherein the botanical extract has a flavonoid content of at least about twenty times greater than that of the fruit of *Vaccinum macrocarpon*.

2. The method according to claim 1, wherein the botanical extract of the leaf of *Vaccinium macrocarpon* inhibits γ-H2AX activity, thereby inhibiting oxidation-induced DNA damage in said subject.

3. The method according to claim 1, wherein the composition is administered in form for oral ingestion.

4. The method according to claim 1, wherein the composition is a dietary supplement.

5. The method according to claim 4, wherein the dietary supplement is in solid dosage form.

* * * * *